(12) United States Patent
Knill et al.

(10) Patent No.: US 9,050,443 B2
(45) Date of Patent: Jun. 9, 2015

(54) WOUND DRESSING

(75) Inventors: Esther Knill, Winterthur (CH); Regina Bruggisser, Winterthur (CH)

(73) Assignee: IVF HARTMANN AG, Neuhausen am Rheinfall (CH)

( * ) Notice: Subject to any disclaimer, the term of this patent is extended or adjusted under 35 U.S.C. 154(b) by 241 days.

(21) Appl. No.: 13/697,273

(22) PCT Filed: May 10, 2011

(86) PCT No.: PCT/EP2011/057491
§ 371 (c)(1),
(2), (4) Date: Dec. 26, 2012

(87) PCT Pub. No.: WO2011/141454
PCT Pub. Date: Nov. 17, 2011

(65) Prior Publication Data
US 2014/0163485 A1    Jun. 12, 2014

(30) Foreign Application Priority Data
May 11, 2010  (DE) .......................... 10 2010 020 050

(51) Int. Cl.
*A61F 13/00* (2006.01)
*A61M 35/00* (2006.01)
(Continued)

(52) U.S. Cl.
CPC .......... *A61M 35/00* (2013.01); *A61F 13/00063* (2013.01); *A61F 13/069* (2013.01); *A61F 2013/00217* (2013.01); *A61F 2013/00246* (2013.01); *A61F 2013/00744* (2013.01); *A61F 2013/00753* (2013.01);
(Continued)

(58) Field of Classification Search
CPC ................ A61F 13/00063; A61F 2013/00753; A61L 2300/206
See application file for complete search history.

(56) References Cited

U.S. PATENT DOCUMENTS

| | | | |
|---|---|---|---|
| 6,613,347 B2* | 9/2003 | Drury | 424/443 |
| 8,383,527 B2* | 2/2013 | Hilfenhaus et al. | 442/123 |
| 2001/0009711 A1* | 7/2001 | Latimer et al. | 428/182 |

(Continued)

FOREIGN PATENT DOCUMENTS

| | | |
|---|---|---|
| DE | 601 26 506 T2 | 11/2007 |
| DE | 102007030931 A1 | 1/2009 |

(Continued)

OTHER PUBLICATIONS

"Today's Wound Care Treatments," Medline Industries Inc., Nov. 2013.*

*Primary Examiner* — Susan Su
(74) *Attorney, Agent, or Firm* — Henry M. Feiereisen LLC

(57) ABSTRACT

A wound dressing for wound treatment in a moist or wet milieu includes a fibrous non woven fabric-based suction-/rinsing body, a superabsorbent material distributed in the suction-/rinsing body and including negative groups, a saline aqueous solution including an antimicrobially acting substance which is cationic at pH values of 4-7.5 of the moist or wet milieu, wherein the antimicrobially acting substance is attracted and retained by the negative groups of the superabsorbent material, and is supplied to the suction-/rinsing body by the manufacturer, and a cover forming outer visible sides of the wound dressing, wherein an atraumatically acting coating is applied in some regions and in a structured manner on one of the outer visible sides which faces toward the wound, with a degree of coverage of at most 70%.

18 Claims, 2 Drawing Sheets

(51) Int. Cl.
*A61L 15/46* (2006.01)
*A61F 13/06* (2006.01)

(52) U.S. Cl.
CPC .............. *A61F 2013/00855* (2013.01); *A61F 2013/0091* (2013.01); *A61L 15/46* (2013.01); *A61L 2300/206* (2013.01)

(56) References Cited

U.S. PATENT DOCUMENTS

| | | | |
|---|---|---|---|
| 2002/0137418 A1* | 9/2002 | Seth | 442/334 |
| 2003/0208178 A1* | 11/2003 | Edens et al. | 604/385.17 |
| 2004/0142019 A1 | 7/2004 | Serafica et al. | |
| 2006/0141891 A1* | 6/2006 | Melius et al. | 442/416 |
| 2007/0255193 A1 | 11/2007 | Patel et al. | |
| 2008/0082059 A1 | 4/2008 | Fink et al. | |
| 2009/0035342 A1* | 2/2009 | Karandikar et al. | 424/411 |
| 2009/0263469 A1 | 10/2009 | Rohrer et al. | |
| 2010/0262090 A1* | 10/2010 | Riesinger | 604/304 |
| 2011/0171283 A1 | 7/2011 | Riesinger | |
| 2012/0156274 A1 | 6/2012 | Fugmann et al. | |

FOREIGN PATENT DOCUMENTS

| | | |
|---|---|---|
| EP | 0 594 034 B1 | 10/1993 |
| EP | 342950 B1 * | 8/1994 |
| EP | 251810 B2 * | 9/2001 |
| EP | 2 001 440 B1 | 3/2007 |
| EP | 2072063 A1 | 12/2007 |
| WO | WO 2006/066752 A1 | 6/2006 |
| WO | WO 2008/037082 A1 | 4/2008 |

* cited by examiner

WOUND DRESSING

CROSS-REFERENCES TO RELATED APPLICATIONS

This application is the U.S. National Stage of International Application No. PCT/EP2011/057491, filed May 10, 2011, which designated the United States and has been published as International Publication No. WO 2011/141454 and which claims the priority of German Patent Application, Serial No. 10 2010 020 050.6, filed May 11, 2010, pursuant to 35 U.S.C. 119(a)-(d).

BACKGROUND OF THE INVENTION

The invention relates to a wound dressing for treating wounds in the moist or wet milieu, with a fibrous nonwoven fabric based suction/rinsing body in which super absorbent material is distributed, wherein the suction/rinsing body is supplied by the manufacturer with a saline aqueous solution, in particular Ringer's solution, preferably to the point of saturation, and with an outer cover which forms the outer visible sides of the wound dressing, wherein on the side of the suction/rinsing body which faces away from the wound, an evaporation-inhibiting film layer can be provided.

Such a wound dressing is known to the applicant from EP 0 594 034 B1. This is a wound cushion type or compress like wound dressing which can be placed on a wound or can also be used for tamponading deep wounds. The suction/rinsing body is soaked by the manufacturer preferably until saturation with a saline aqueous solution which swells the superabsorbent material and converts the latter into a gel like state. This gives the suction/rinsing body a dual function in wounds with strong exudation. Wound secretions are actively absorbed by the suction/rinsing body including their critical components such as germs, and held in the suction/rinsing body, wherein the suction/rinsing body in return gives off the saline aqueous solution to the wound and in this way creates or supports a moist wound milieu. By this, the wound cleaning and a positive wound conditioning is supported and the healing positively influenced. This is referred to as interactive wet therapy which is used in particular in the case of poorly healing wounds in clinically manifest infected wounds or in chronic wounds with different causes such as diabetic gangrene, ulcus decubitus or ulcus cruris.

The aforementioned Ringer's solution is typically an aqueous solution containing sodium chloride, potassium chloride and calcium chloride (in particular 8.6 g NaCl, 0.3 g KCl and 0.33 g CaCl2 per liter).

The time-interval for changing, i.e., the time of use of a wound dressing until the next bandage change, should be at least 24 h, wherein an increase of the change intervals in particular to 48 to 72 h is sought. This would be desirable for economic reasons but also for reasons of interference with the wound healing caused by frequent bandage changes. On the other hand, there is a risk in this case that this would negatively affect wound conditioning which is the reason why previously the changing intervals in the interactive wet therapy were kept in the range of 24 h.

SUMMARY OF THE INVENTION

The present invention is based on the objective to improve a wound dressing of the type described at the beginning with regard to optimizing the wound conditioning, in particular with regard to enabling an extension of the time-interval for changing. According to the invention, this object is solved with a wound dressing of the mentioned type in that the aqueous solution includes an antimicrobially acting substance which is cationic at pH values of 4-7.5 of a typical moist or wet wound milieu, and is attracted by the negative groups of the anionic superabsorbent material and in this way acts antimicrobially inside the suction/rinse body, and in that on the side which faces the wound, the cover is provided in some regions and in a structured manner with an atraumatically acting coating, with a degree of coverage of at most 70%.

Previously, substances with antimicrobial effect were not used in suction/rinsing bodies of wound dressings because the wound was sought to be kept free of such substances or an antiseptic was intentionally applied directly into the wound. With the present invention, it was recognized that during operation, cationic substances with antimicrobial effect are bound and thus retained by negative groups of typical superabsorbent materials in such a manner, that they mostly remain in the suction/rinsing body, i.e., they do not or only to an insignificant degree enter the wound also when operating the suction/rinsing body of a wound dressing according to the invention in the liquid-exchanging mode in the moist or wet wound milieu. Thus, an excellent conditioning of the suction/rinsing body also for applications beyond 24 h can be realized, which in turn has an advantageous effect on the conditioning of the wound milieu, since through the exchange of liquid during operation of the suction/rinsing body, liquid reaches the wound from the optimally antimicrobially conditioned suction/rinsing body, however, essentially without septically acting substances or germs reentering the wound. A recontamination is thus mostly prevented.

The atraumatically acting coating which is applied in some regions and in a structured manner to the side which faces toward the wound, unexpectedly achieves a better exchange of liquid via the coating-free areas, because adhesion between the cover of the wound dressing and the wound tissue over a continuous area is prevented by the adjoining atraumatically coated areas due to a spacer function in the atraumatically coated areas. This leads to an overall improved exchange of liquid which in turn has a beneficial effect on the wound healing in combination with the antimicrobially acting cationic substance inside the suction/rinsing body, because wound secretions/exudates together with germs can enter the suction/rinsing body to a greater degree, where they can be treated antimicrobially. The term of a coating which is applied in some regions and in a structured manner implies that it is not a coating which has a continuous planar extension but rather a porous coating as it can be realized by points, islands, lines, strips or other connected or unconnected structures.

Preferably, the anionic superabsorbent material is a polymer, in particular a polymer which is at least partially cross linked, in particular on a polyacrylate basis. According to another embodiment, the anionic super absorbent material is a polysaccharide such as for example starch or a polysaccharide derivate for example carboxylated polysaccharides as described in WO-A-2008/037082.

The antimicrobially acting cationic substance can for example be substances with amino or imino groups which are cationically charged in a solution with a pH value of 4 to 7.5. Further, the cationic substance can be antimicrobially acting metal cations, in particular silver cations, for example a complex of 1-vinyl-2-Pyrrolidon with silver cations. Particularly suited antimicrobially acting cationic substances are biguanide-derivates such as chlorhexidine or polybiguanide, such as polyethylene biguanide (PEB), polytetramethylenbiguanide (PTMB) or polyethylenhexamethylenbiguanide (PE- HMB). A particularly preferred polybiguanide is polyhexamethylenbiguanide (PHMB, or polyhexanide). Further suited antimicrobially acting cationic substances are polyguanidine, such as for example polyhexamethylenguanide (PHMG), N-Octyl-1-[10-(4-Octyliminopyridine-1-yl)decyl]pyridine-4-imine (Ocenedine), quarternary amino compounds such as for example benzalkoniumchloride or cetylpyridiniumchloride, triazines such as for example 1-(3-chlorallyl)-3,5,7-triaza-1-azoniaadamantane-chloride or the ammonia compound taurolidine. The concentration of the antiseptically acting additive in the aqueous solution which is then used for activating the dry suction/rinsing body is preferably 0.06-0.20 weight %, in particular 0.08-0.15 weight %, in particular 0.10-0.15 weight % (with regard to the aqueous solution prior to activation of the suction/rinsing body).

As already explained above, the choice of the antimicrobially acting substance in combination with the super absorbent material achieves that this substance is to the greatest degree or mostly retained in the suction/rinsing body also during operation of the wound dressing. This can be visually tested or verified by way of the Hemmhoftest (English: zone of inhibition test). When carrying out the zone of inhibition test which is described in detail below, it can be visually tested whether germicidal substances are released from a test body in significant amounts. When they are released they kill or inhibit the growth of so called colony forming units in an environment of the test body which can be determined by visual inspection of the test body and its environment. When no such environment i.e, zone of inhibition is detectable this means that substances which significantly inhibit the colony growth were not released from the test body to a significant degree. For further characterizing the subject matter of the present invention, the wound dressing is further characterized in that when performing the zone of inhibition test a release of antimicrobially acting cationic substance from the wound dressing cannot be detected visually. This means that a zone of inhibition cannot be visually detected when performing the test which is described in the following.

Zone of Inhibition Test

For performing the zone of inhibition test, a wound dressing of the type at issue is placed on a previously prepared agar plate. For this, an agar plate with a diameter 8.5 cm is used, which each contained 15 ml caseinpeptone-soypeptone-agar (concentration of the casein peptone-soy-peptone: 40 g/l). On this agar plate, 100 µl of a staphylococcus aureus ATCC 6538 germ suspension (approximately $5 \times 10^6$ colony forming units/ml) were streaked with a cotton stick and dried for 10 to 15 min. After the drying of the germ suspension with closed lid the sterilized test body, which however was cooled to room temperature, is placed in the form of the wound dressing to be tested on the agar plate with the side which faces the wound (reference sign 8 in FIG. 1). The plate is then incubated upright for 18 h at 35° C. After this, the agar dish was inspected visually for the formation of an inhibition zone. The inhibition zone is typically calculated in millimeters according to the formula $H=(D-d):2$, wherein D is the total diameter of test body and zone of inhibition and d the diameter of the test body in each case in millimeters. When a zone of inhibition cannot be detected around the test body (D=d and H=0), the release of possible substances from the test body and their effect on the colony growth cannot be detected by way of the zone of inhibition test.

The composition of the suction/rinsing body can suitably include: a superabsorbent material of the above mentioned type in an amount of 120-170 g/m², cellulosic fibers in an amount of 5-18 g/m². In addition, a tissue layer can be provided on one or both sides. The suction/rinsing body can be composed of the previously mentioned components (and in addition of the saline aqueous solution).

With regard to an interval time for changing which is as long as possible, it is relevant that sufficient liquid is available in the suction/rinsing body over the entire duration of use, i.e., until the next bandage change, in order for the dual function of the suction/rinsing body to actually come into effect. For this, the evaporation of the liquid during use of the wound dressing has to be kept within acceptable limits. With regard to this, it is advantageous when the cover has a non woven fabric which has a film layer laminated onto its outside which inhibits evaporation. It has been shown that this allows significantly reducing evaporation compared to previous wound dressings with garment-protecting films which are arranged inside the cover on the side of the suction/rinsing body which faces away from the wound, or compared to inserted garment-protecting films.

Preferably, the nonwoven fabric is a polyoleine-nonwoven fabric, in particular a polypropylene nonwoven fabric. The cover on the side of the wound dressing which faces toward the wound but generally also on the side of the wound dressing which faces away from the wound can advantageously be a textile flat material such as for example a crocheted fabric, a knitted fabric or a woven fabric, in particular made of polyolefin, in particular made of polypropylene. In any case, the use of a cover in form of a textile fabric, in particular crocheted fabric, knitted fabric or woven fabric on the side which faces toward the wound is preferred with regard to the liquid exchange i.e., with regard to the dual function of the suction/rinsing body.

The above mentioned advantageous aspects of the atraumatically acting coating which is applied in some regions in a structured manner, namely preventing sticking to the wound tissue and providing a certain spacer function, are particularly well achieved by a silicone coating. When the atraumatically acting coating is applied on a textile fabric in the form of silicone as previously mentioned, a particularly advantageous composite results with regard to flexibility, suppleness and effectiveness.

Further, a degree of coverage of the atraumatically acting coating which is applied in some regions in a structured manner, of 40 to 70%, in particular of 40-60% and further in particular of 40-55 Weight % in particular 40-50% of the surface of the observed cover which faces toward the wound, is advantageous.

The overhang of the coating in Z-direction over the plane of the outside of the cover is preferably 0.03-0.5 mm, in particular 0.1-0.4 mm, 0.1-0.3 mm, in particular 0.1-0.2 mm. The atraumatically acting coating which is applied in some regions in a structured manner, preferably has a dimension in at least one plane direction of at most 4 mm, in particular of at most 3 mm and further in particular of 1-3 mm, in particular of 2-3 mm.

The distance of neighboring surface areas to one another is preferably at least 1 mm and at most 5 mm.

With regard to the formation of the fibrous non woven fabric based suction/rinsing body it is advantageous when cellulosic fibers, preferably air-laid cellulosic fibers or preferably air-laid mixtures of cellulosic fibers and thermoset fibers, in particular polyolefin fibers, in particular polypropylene or polypropylene/polyethylene fibers are used which preferably form the entire fibrous base of the suction/rinsing body. The proportion of the thermoset fibers of such a fiber mixture is preferably only about 5-10% of the proportion of cellulosic fibers.

It is further advantageous when the surface specific evaporation rate in the time interval 24 h to 72 h after the simulated application of the wound dressing <0.02 g/24 h·cm$^2$, in particular <0.017 g/24 h·cm$^2$, in particular <0.015 g/24 h·cm$^2$, in particular <0.012 g/24 h·cm$^2$. For this the following testing method is used Test-Method Evaporation Rate:

For determining the evaporation rate, a wound dressing 20 which is initially packaged water vapor tight (FIG. 2) is removed from its packaging. It has a fibrous non woven fabric based suction/rinsing body with super absorbent material, in particular Favor pac 300 from the company Evonik Stockhausen GmbH, and typically cellulosic fibers and, as the case may be, also thermoset fibers. Prior to the water vapor tight packaging, the wound dressing 20 was activated with saline aqueous solution, in particular Ringer's solution. This wound dressing 20 is then placed on a water vapor impermeable packaging film 22 with its side which faces toward the wound (reference sign 8 in FIG. 1) and a circumferential border area 24 is covered with a film 26 and in thereby fixed against the support (simulated application of the wound dressing). For this, a film 26 (for example of the trade mark Opsite flexifix) is then spread over the wound dressing 20 and an opening 28 is cut into the center of the cover film 26 as schematically shown in FIG. 2, so that the predominant portion of the surface 30 of the wound dressing 20 is exposed to the environment and only the circumferential border region 24 remains covered at a width of 5 mm by the cover film 26. In this way, the predominant portion of the side of the wound dressing which faces away from the body is exposed to the environment, so that liquid which was taken up by the suction/rinsing body can evaporate over this surface. The corresponding sample is stored at 23° and 50% relative humidity and weighed at defined time points, namely t=0 h, t=24 h, t=48 h and t=72 h. By determining the difference in weight, the evaporation rate can then be given in g/24 h or in g/24 h cm$^2$. The latter value is a surface specific evaporation rate which relates to the exposed surface.

It is further advantageous when the surface-specific evaporation within the first 24 h after the simulated application of the wound dressing is <0.050 g/24 h cm$^2$ liquid, in particular <0.037 g/24 h·cm$^2$ liquid, in particular <0.025 g/24 h·cm$^2$.

BRIEF DESCRIPTION OF THE DRAWING

Further features, details and advantages of the invention result from the included patent claims and from the drawings and the following description of a preferred embodiment of the wound dressing according to the invention. In the drawing it is shown in:

DETAILED DESCRIPTION OF PREFERRED EMBODIMENTS

Figure 1:
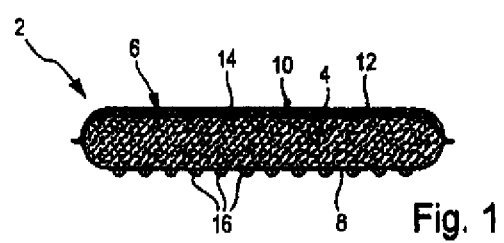
FIG. 1 a highly schematic sectional view of a wound dressing according to the invention.
Figure 2:
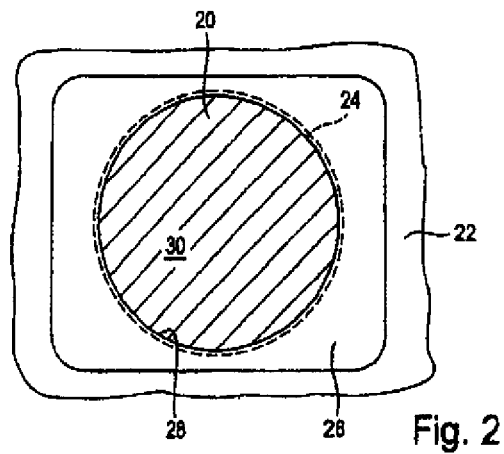
FIG. 2 the arrangement for performing the test for determining the evaporation rate.

FIG. 1 shows a section of a wound dressing 2. It includes a suction/rinsing body 4 on fiber non woven fabric basis. This fiber basis is a preferred mixture of air laid cellulosic fibers (cellulose) and polypropylene fibers or polypropylene/polyethylene fibers. Added to this fiber mixture are superabsorbent polymer material (SAP) in particle form or in fiber form as homogenous as possible where in the SAP proportion of the total mass of the suction/rinsing body is preferably 40-50 weight %. The mean grain size of the SAP particle is for example 150 to 850 um (for example polyacrylate of the trade mark Favor pac 300 of the company Evonik Stockhausen GmbH).

The suction/rinsing body 4 is surrounded by a cover 6 which forms the outsides of the wound dressing, which cover 6 is formed by a cover layer 8 which faces toward the wound and a cover layer 10 which faces away from the wound, which are connected at their borders. The cover layer 8 which faces toward the wound is preferably a knitted fabric, preferably made of polypropylene, wherein a woven fabric or a crocheted fabric is also advantageously conceivable, i.e. a cover layer made of threads or filaments with textile connection which enables a good exchange of liquid between suction/rinsing body 4 and the wound environment.

The cover layer 10 which faces away from the wound is formed by a surface composite or surface laminate, namely by a non woven fabric 12, preferably made of polypropylene and a germ and water tight film 14 laminated thereon, which film extends over the entire surface extension of the non woven fabric 12 and offers a significantly improved evaporation protection toward the side which faces away from the wound.

On the outside which faces toward the wound of the cover layer 8 which faces toward the wound, an atraumatically acting coating 16 is provided which is applied in some regions and in a structured manner. This coating is preferably a silicone coating, wherein the coating is porous and in the exemplary shown case is formed by a plurality of relatively thin strips or lines or by regions in the form of islands, which regions are separated from one another by uncoated regions. In these uncoated regions the cover layer which faces toward the wound is exposed to the wound. In this respect, the atraumatically acting coating 16 forms an overhang in the size range mentioned in the introduction of the description, whereby on one hand a sticking of the cover layer 8 to wound tissue can be prevented and on the other hand a certain small distance between the cover layer which faces towards the wound, and the wound tissue can be maintained, whereby the porous cover layer material remains three dimensionally open and provides or maintains a small resistance for passage of liquid in both directions over the time of use of the wound dressing.

The wound dressing 2 further has a border which extends in circumferential direction, and is formed by the cover layers 8, 10 which are welded together at the border. The wound dressings are however punched so that the border is mostly negligible.

The previously described atraumatically acting coating 16 is not applied in the endless flat material of the cover layers but only after the last welding process, in particular after separation of the wound dressing products, i.e., after the respective suction/rinsing bodies 4 are fixed to one another by joints between the cover layer 8 which faces toward the wound and the cover layer 10 which faces away from the wound. The thus produced product arrangement or the already separated product punch-pieces are then coated in some regions and in a structured manner with coating material in the previously described manner, preferably with 1-component silicone from a dispenser device. For this, a dosing device with an accurately ending needle-shaped dosing nozzle is used, which includes a valve which opens and closes in a controlled manner. The dosing device is movable in X and Y direction and preferably also in Z-direction in a programmable controlled manner. In this way, an application in some regions in a structured manner, in particular with the previously stated parameters, with regard to the dimension and the overhang of the coated surface regions can be achieved.

Only then the suction/rinsing body 4 of the wound dressing according to the invention is supplied with saline aqueous solution, in particular Ringer's solution, preferably to the point of saturation. This saline solution is an antimicrobially acting substance, which is cationic in the moist or wet wound milieu at pH values in the slightly acid to neutral range from 4 to 7.5. This antimicrobially acting cationic substance is attracted by negative groups of the anionic superabsorbent material so that the substance remains bound to the superabsorbent materials also in the liquid exchanging operation of the suction/rinsing body 4, i.e. the substance is to the greatest extent not released into the wound milieu. This prevents germs which are carried into the suction/rinsing body 4 along with wound secretion from propagating, which prevents a recontamination in the direction toward the wound to the greatest possible extent. It has been shown that such a microbiological recontamination could be prevented to the greatest possible extent over 72 h, which is attributed to the fact that the antimicrobial substance is retained evenly distributed within the suction/rinsing body 4, bound to the superabsorbent materials due to the substance's cationic state.

In a preferred exemplary composition of the wound dressing 2, the fibrous non woven fabric basis of the suction/rinsing body 4 is made of 127 g/m² cellulose fibers (cellulose), 8 g/m² polypropylene/polyethylene fibers as binding fibers (in particular E-505/FV from the company Schwartswalder). To this fiber mixture, 127 g/m²·of the above mentioned superabsorbent polymer materials (SAP) are homogenously added. The thus obtained mixture (fibrous non woven fabric basis+SAP) which forms the suction/rinsing body 4, can further be surrounded by a cellulosic tissue layer which in particular has a surface weight of for example 18 g/m² on each side (Diaper Tissue 1800 from Swedish Tissue AB) (not shown in the Figure); this however, is not strictly necessary. The wound dressing can for example be configured round, with an exemplary dimension of the suction/rinsing body 4 of 5.5 cm diameter, which essentially corresponds to the dimension of the wound dressing 2. The wound dressing 2 was activated with 13.6 ml Ringer's solution, which in the present case essentially corresponds to a saturation of the suction/rinsing body with liquid. The cover 6 is configured as previously described. —In such a wound cover, an evaporation rate during the first 24 h after the simulated placement of 0.19 g/24 h was determined. In this case, an advantageous upper limit would be 0.8 g/24 h, in particular 0.6 g/24 h, in particular 0.4 g/24 h. During the subsequent time interval of 24 h to 72 h the evaporation was 0.16 g/24 h. An advantageous upper limit in this case would be 0.3 g/24 h, in particular 0.2 g/24 h.

Measurement of Separation-Force:

It was noted that the detachability or removability of the wound dressing when changing the bandage, represents a very important property, because an excessive adhesion or even sticking to the wound base causes pain during detachment and leads to further damage to the wound base. The measurement of separation force described in the following is used to determine the tendency of sticking to the wound base and therefore allows an assessment regarding the detachability or removability of a wound dressing from the wound:

The measurement of the separation force between a textile substrate and gelatin serves as a measure for the detachability or removability. The textile substrate is the textile surface layer of the wound dressing which contacts the wound, and the gelatin is to simulate the wound medium or the skin surface.

An aqueous, 20% gelatin solution is prepared (keep ca. 1.5 h at 60° C. to dissolve the gelatin); after this, 100 ml of this is poured into a petri dish. After a 30 min. cooling period, the samples to be tested (size 2.5 cm×10 cm) are respectively placed onto the gelatin in the petri dish and weighted with weights (20 mm×90 mm, 4.2 g). Subsequently, the gelatin plates are incubated for 3 h at 36° C. and 50% relative humidity. For the force measurement, the gelatin plates are acclimatized for 1 h at 23° C. and 50% relative humidity.

For measuring the separation force, a respective sample end is slightly detached from the gelatin bed and extended with an adhesive tape. The petri dish and the end of the adhesive tapes are fixed in the mounting of the tensile test device after which the separation force is measured. The pulling of the tensile test device is roughly vertical while the respective gelatin plate/petri dish is arranged horizontally. Analyzed is the mean separation force over the measured displacement.

Figure 3:
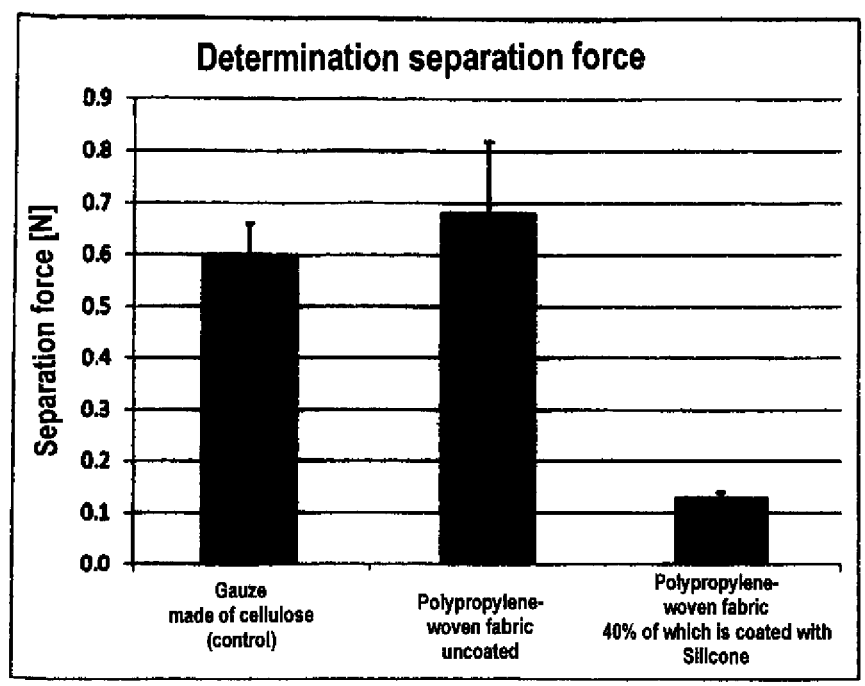
FIG. 3 shows the result of measurements.

FIG. 3 shows the result of measurements of the following samples: the separation force was on one hand determined at a polypropylene-knitted fabric, whose surface was coated to 40% with silicone. The silicone was applied punctiform.

Uncoated polypropylene knitted fabric and gauze were used as control samples.

It can be seen that the silicone coated polypropylene knitted fabric is significantly better suited as cover of the suction/rinsing body on the side which faces the wound than gauze or uncoated polypropylene knitted fabric.

Observational Study

The applicant has performed a clinical observational study. The wound dressing had the composition described above with an atraumatically acting coating in the form of silicone applied punctiform in a structured manner with a degree of coverage of 40% of the surface of the cover layer 8 which faces the wound. The saline aqueous solution of the suction/rinsing body 4 was Ringer's solution with 0.1 weight % PHMB as antimicrobially acting cationic substance.

The observational study included the time period of the initial examination E with a first application of the wound dressing until the final examination A with a change of the wound dressing. In the intermediate time period two further bandage changes were performed.

The initial examination was performed on 66 patients. The documentation of three successive bandage changes was planned per patient. 3 patients were no longer available at the time point of the first bandage change. 4 further patients were no longer available for the observational study at the time point of the second bandage change. The final examination was performed on 59 patients. Where possible, it was nevertheless attempted to obtain a final product assessment and to include the latter in the evaluation. For the final product evaluation, 63 patients where thus available.

50% of the patients (33) were male or, respectively female.

The average age of all patients was about 75 years. The average weight of the patients was about 77 kg, minimum 43.5 kg, maximum 122.0 kg, median 78 kg. The average height was 1.69 m, minimum 1.48 m, maximum 1.92 m, median 1.68 m. the causes for the wounds were divided as follows:

| Cause | Number (n) | Proportion (%) |
| --- | --- | --- |
| Ulcus cruris venosum | 10 | 15.2 |
| Ulcus cruris arteriosum | 6 | 9.1 |
| Ulcus cruris mixtum | 10 | 15.2 |
| Decubitus | 19 | 28.8 |

-continued

| Cause | Number (n) | Proportion (%) |
|---|---|---|
| Pressure ulcus in diabetes | 9 | 13.6 |
| Diabetic gangrene | 4 | 6.1 |
| Traumatic wound | 3 | 4.5 |
| Other | 5 | 7.6 |

The average length of the wounds at the beginning of the treatment, was 5.26±3.08 cm (minimum 0.5 cm, maximum 16.0 cm, median 4.0 cm) the average width was 3.94±2.08 cm (minimum 0.3 cm, maximum 10.0 cm, median 4.0 cm). In one case no wound size was given.

For 58 wounds, information regarding the wound depth was also available. The average wound depth was 0.93±0.1 cm (Minimum 0.1 cm, maximum 5.5 cm, median 0.5 cm).

The remaining wounds are superficial wounds.

At the beginning of the observational study, the wounds had been present for 1.3±3.5 years (minimum 0 day, maximum 20.0 years, median 4.0 months). For 7 patients no information regarding the age of the wound was available.

6 wounds (9.1%) did not exude, 19 (28.8%) little, 28 (42.4%) moderate, 12 (18.2%) strongly and 1 (1.5%) very strongly.

12 wounds (18.2%) showed signs of infection at the beginning of the observational study.

Times between the bandage changes: in the following table the times between the bandage changes and the overall duration of the observational study in days is compiled. Patients, for which due to the time between the documented bandage changes it can be relatively safely assumed that the bandage changes were not successive bandage changes, were not taken into account.

| | E to 1. VW | 1. VW to 2. VW | 2. VW to A | E to A all* | E to A 3 VW** |
|---|---|---|---|---|---|
| Average | 2.59 ± 0.93 | 2.64 ± 0.94 | 2.71 ± 0.87 | 7.48 ± 2.45 | 7.80 ± 2.36 |
| Minimum | 1 | 1 | 1 | 3 | 3 |
| Maximum | 6 | 6 | 5 | 12 | 12 |
| Median | 3 | 3 | 3 | 8 | 9 |

E = initial examination, VW = bandage change, A = final examination
E = initial examination, VW = bandage change, A = final examination
E to A all: here, patients in which the observational study was terminated prematurely already after the first or second bandage change were also included
**E to A 3 VW: here, only patients who finished the observational study according to plan after the 3. bandage change were taken into account Pain During Bandage Change In the following table, the number of the patients experiencing pain during the bandage change is shown

| | Initial examination | | 1. Bandage change | | 2. Bandage change | | Final examination | |
|---|---|---|---|---|---|---|---|---|
| | number | % | number | % | number | % | number | % |
| No pain at VW | 31 | 47.0 | 36 | 57.1 | 36 | 61.0 | 36 | 57.1 |
| Light pain at VW | 15 | 22.7 | 17 | 27.0 | 15 | 25.4 | 21 | 33.3 |
| Moderate pain At VW | 16 | 24.2 | 7 | 11.1 | 6 | 10.1 | 5 | 7.9 |
| Strong pain at VW | 4 | 6.1 | 3 | 4.8 | 2 | 3.4 | 1 | 1.6 |

A significant improvement of the experienced pain during bandage change can be seen between the time point of the initial examination and the time point of the final examination which is also attributed to the improved detachability/removability of the used wound dressing of the components of the wound dressing, which in turn is attributed to an interaction of the components of the wound dressing and overall positively supports the wound healing.

Removability of the Wound Dressing

The wound dressing could be removed very well (48.4%) or well (46.9%) from the wounds in 95.3% of the cases. Because the issue of removability is very important and may also be influenced by the wear time of the wound cushion, the removability was also examined after each individual bandage change. No problems were encountered in any of the cases when removing the wound cushion. However, it could be observed that the wound cushions sometimes slightly stuck on the wounds (3.8%-9.1%-17.5%) after being worn for a longer time (one, two or three days). However, they were still always removable without problems. Even after a wearing time of three days, no sticking was observable in 82.5% of the cases.

These results allow the conclusion that the wound dressing does not stick to the wound even after a wearing time of three days.

Moisture of the Wound Cushion

In 54 of 63 cases (85.7%) the wound cushion was still optimally moist at bandage change. In 6 cases (9.5%) the wound cushion was still sufficiently moist, the user however, would have expected more. 3 times the users perceived the moisture as no longer optimal, a wound cushion which was clearly too dry was observed in no case.

Signs of Infection 7 of 63 wounds (11.1%) for which information was available at this point showed signs of a wound infection at the time point of the final evaluation.

Drapeability

Drapeabiltiy relates to the adaptability of the wound dressing to the wound base; this is intended to prevent detaching of the wound dressing. At the beginning of the observational study the drapeability of the used wound dressing was assessed 14 times as very good (21.2%), 44 times as good (66.7%) 7 times as satisfactory (10.1%) once as sufficient (1.5%) and in no case as inadequate.

Wound Condition Compared to the Beginning of the Study

For 62 patients an evaluation of the wound compared to the beginning of the study was available. The following picture emerges

| Condition | Number | Proportion (%) |
|---|---|---|
| Significantly improved | 15 | 24.2 |
| Improved | 34 | 54.8 |
| Unchanged | 7 | 11.3 |
| worsened | 1 | 1.6 |
| Significantly worsened | 5 | 8.1 |

Overall Impression

In the observational study, the overall impression of the wound dressing was evaluated as very good or good in 87.3% of all cases. This positive impression was also confirmed by the fact that the expectations toward the new product were exceeded, met or predominantly met in 87.5% of the cases.

The invention claimed is:
1. A wound dressing for wound treatment in a moist or wet milieu, comprising:
a fibrous non woven fabric-based suction-/rinsing body;
a superabsorbent material distributed in the suction-/rinsing body and comprising negative groups;

a saline aqueous solution including an antimicrobially acting substance which is cationic at pH values of 4-7.5 of the moist or wet milieu, said antimicrobially acting substance being attracted and retained by the negative groups of the superabsorbent material, said saline aqueous solution being supplied to the suction/rinsing body by a manufacturer; and a cover forming outer visible sides of the wound dressing, wherein an atraumatically acting coating is applied in some regions and in a structured manner on one of the outer visible sides which faces toward the wound, with a degree of coverage of at most 70%, wherein a distance of neighboring coated surface areas to each other is at least 1 mm and at most 5 mm.

2. The wound dressing of claim 1, wherein the saline aqueous solution is supplied to the suction/rinsing body to a point of saturation.

3. The wound dressing of claim 1, wherein the saline aqueous solution is Ringer's solution.

4. The wound dressing of claim 1, further comprising an evaporation-inhibiting film layer provided on a side of the suction/rinsing body which faces away from the wound.

5. The wound dressing of claim 4, wherein another side of the cover which faces away from the wound is provided with a non woven fabric, and wherein a film layer which is laminated on an outside of the non woven fabric, said film layer forming the evaporation-inhibiting film layer.

6. The wound dressing of claim 5, wherein the non woven fabric is a polyolefin-non woven fabric.

7. The wound dressing of claim 1, wherein the antimicrobially acting substance is a biguanide.

8. The wound dressing of claim 1, wherein a concentration of the antimicrobially acting substance in the saline aqueous solution is 0.06-0.20 weight %.

9. The wound dressing of claim 1, wherein a release of the antimicrobially acting substance from the wound dressing is visually undetectable in a zone of inhibition test.

10. The wound dressing of claim 1, wherein the cover on the side of the wound dressing which faces toward the wound and/or on the side of the wound dressing which faces away from the wound is formed by a textile flat material.

11. The wound dressing of claim 1, wherein the atraumatically acting coating is a silicone coating.

12. The wound dressing of claim 1, wherein the degree of coverage of the atraumatically acting coating (16) is 40-70%.

13. The wound dressing of claim 1, wherein the atraumatically acting coating forms an overhang (in Z-direction) over a plane of the outside of the cover of 0.03-0.5 mm.

14. The wound dressing of claim 1, wherein the atraumatically acting coating has a dimension in at least one planar direction of at most 4 mm.

15. The wound dressing of claim 1, wherein the suction-/rinsing body includes cellulosic fibers and thermosetting fibers.

16. The wound dressing of claim 1, wherein a surface specific evaporation rate in a time interval 24 h to 72 h after a simulated application of the wound dressing is <0.020 g/24 h cm$^2$.

17. The wound dressing of claim 1, wherein the surface specific evaporation rate within 24 h after the simulated placement of the wound dressing is <0.050 g/24 h cm$^2$ liquid.

18. The wound dressing of claim 1, having a dimension in at least one planar direction of 2-30 cm.

* * * * *